United States Patent
Do et al.

(10) Patent No.: US 11,660,464 B2
(45) Date of Patent: May 30, 2023

(54) LIGHTING DEVICE FOR BRIGHT THERAPY AND DARK THERAPY

(71) Applicant: Kookmin University Industry Academy Cooperation Foundation, Seoul (KR)

(72) Inventors: Young Rag Do, Seoul (KR); Changwook Kim, Seoul (KR); Yun Jae Eo, Seoul (KR)

(73) Assignee: Kookmin University Industry Academy Cooperation Foundation, Seoul (KR)

( * ) Notice: Subject to any disclaimer, the term of this patent is extended or adjusted under 35 U.S.C. 154(b) by 378 days.

(21) Appl. No.: 16/943,707

(22) Filed: Jul. 30, 2020

(65) Prior Publication Data

US 2021/0031050 A1 Feb. 4, 2021

(30) Foreign Application Priority Data

Aug. 2, 2019 (KR) .......................... 10-2019-0094308

(51) Int. Cl.
*A61N 5/06* (2006.01)
*H05B 47/16* (2020.01)
*H05B 45/10* (2020.01)
*H05B 45/20* (2020.01)
*H05B 47/175* (2020.01)
*A61M 21/00* (2006.01)

(52) U.S. Cl.
CPC .......... *A61N 5/0613* (2013.01); *A61M 21/00* (2013.01); *H05B 45/10* (2020.01); *H05B 45/20* (2020.01); *H05B 47/16* (2020.01); *H05B 47/175* (2020.01); *A61M 2021/0044* (2013.01); *A61M 2021/0083* (2013.01); *A61M 2205/051* (2013.01); *A61N 2005/0663* (2013.01)

(58) Field of Classification Search
CPC .......... A61N 5/0613; A61N 2005/0663; H05B 47/175; H05B 45/20; H05B 47/16; H05B 45/10; A61M 21/00; A61M 2021/0044; A61M 2021/0083; A61M 2205/051
See application file for complete search history.

(56) References Cited

U.S. PATENT DOCUMENTS

2016/0316527 A1* 10/2016 Allen ...................... H05B 47/16
2018/0339127 A1* 11/2018 Van Reen ............ A61N 5/0618

FOREIGN PATENT DOCUMENTS

| KR | 100609412 B1 | 8/2006 |
| KR | 1020110021756 | 3/2011 |
| KR | 20170123065 | 11/2017 |
| KR | 20170137446 A | * 12/2017 |
| KR | 1020170137446 | 12/2017 |

* cited by examiner

*Primary Examiner* — Carl H Layno
*Assistant Examiner* — Aya Ziad Bakkar
(74) *Attorney, Agent, or Firm* — K&L Gates LLP

(57) ABSTRACT

Disclosed is a lighting device for bright therapy and dark therapy, comprising: a light source part including a red light source, a green light source and a blue light source; a power supply part supplying a power to the light source part; and a controller adjusting, by controlling the power supply part, a bio illuminance to allow melatonin suppression value to exceed a first reference value during morning hours and to allow the melatonin suppression value to be less than a second reference value while maintaining a visual illuminance over a predetermined value during evening hours.

11 Claims, 5 Drawing Sheets

LIGHTING DEVICE FOR BRIGHT THERAPY AND DARK THERAPY

CROSS-REFERENCE TO RELATED APPLICATION

This application claims priority to and the benefit of Korean Patent Application No. 10-2019-0094308, filed on Aug. 2, 2019, the disclosure of which is incorporated herein by reference in its entirety.

BACKGROUND

1. Field of the Invention

The present invention relates to a lighting device for bright therapy and dark therapy, and more particularly, to a lighting device for both bright therapy and dark therapy capable of accurately controlling a melatonin secretion suppression value (hereinafter referred to as "melatonin suppression value") by adjusting bio-illuminance.

2. Discussion of Related Art

Human beings live with a cycle of one day, which is being called a circadian rhythm, where the circadian rhythm is greatly affected by light.

A day breaks in the morning with the Sun, and the day starts to gradually brighten and then gradually darken in the evening. Concomitant with daily changes of the Sun, various kinds of creatures have changed and adapted along with the Sun for a long time. Under the Sun's circadian influence, human beings also live a circadian life just like the creatures, where the human beings live a daily cycle of waking up and starting daily life when the Sun rises in the morning and taking a rest and sleeping in the evening.

Ever since lighting devices have been invented by Edison, human beings usually live indoors, such as offices, factories, and schools during daytime, and then go to bed after working late in the night under lighted environments, whereby phenomenon occurs in which a circadian rhythm of human beings is broken.

When the circadian rhythm is broken, sleep quality deteriorates and human beings become easily susceptible to various types of diseases such as depression, obesity, and stress associated with the circadian rhythm. Furthermore, destruction of the circadian rhythm over a long period of time increases the likelihood of human beings being inflicted with serious diseases including, but not limited to, cancer and heart diseases.

Since modern people largely live under lighted environments, they cannot sufficiently suppress melatonin secretion in the morning hours due to being exposed to insufficient illumination whereby sufficient melatonin is prevented from being fully secreted at night before sleep by excessively bright illuminances.

Here, the illuminance means an intensity of light perceivable by the human eye, and will be hereinafter referred to as visual illuminance in order to distinguish the same from bio illuminance.

As a result, there is required a need for techniques to change a lighted or lighting environment to a direction that maintains a circadian rhythm, because the lighting destroys people's circadian rhythms.

SUMMARY OF THE INVENTION

It is an object of the present invention to provide a lighting device for bright therapy and dark therapy capable of improving a man's circadian rhythm by suppressing melatonin secretion during morning hours by matching a daily light environment affecting the man's circadian rhythm to a melatonin secretion cycle, and enhancing the man's circadian rhythm by greatly increasing the melatonin secretion during evening hours.

The technical problems to be solved in the present invention are not limited to the technical problems mentioned above, and other technical problems that are not mentioned can be clearly understood by those skilled in the art from the following description.

In order to solve the aforementioned disadvantages/problems, exemplary embodiments of the present invention are to provide a lighting device for bright therapy and dark therapy, the lighting device comprising:

a light source part including a red light source, a green light source and a blue light source;

a power supply part supplying a power to the light source part; and a controller adjusting, by controlling the power supply part, a bio illuminance to allow melatonin suppression value to exceed a first reference value during morning hours and to allow the melatonin suppression value to be less than a second reference value while maintaining a visual illuminance over a predetermined value during evening hours.

Preferably, but not necessarily, the controller may adjust a bio illumination by controlling a visual illumination or a CAF (Circadian Action Factor) of light emitted from the light source part.

Preferably, but not necessarily, the controller may adjust a bio illumination by controlling a visual illumination or a CAF of light emitted from the light source part during the morning hours and by controlling the CAF of light emitted from the light source part during the evening hours.

Preferably, but not necessarily, the controller may adjust the bio illuminance by controlling ON/OFF of the red light source, the green light source and the blue light source, or adjusting the bio illuminance by controlling a current applied to the red light source, the green light source and the blue light source.

Preferably, but not necessarily, the controller may adjust the bio illuminance by controlling a size of current respectively applied to the red light source, the green light source and the blue light source while the size of the current supplied to the light source part is maintained at a predetermined value.

Preferably, but not necessarily, the light source part may further include an orange light source.

Preferably, but not necessarily, the first reference value may be a value selected from within a range of 70%~100%, and the second reference value may be a value selected from within a range less than 30% or less, but excluding 0 (zero).

Preferably, but not necessarily, the controller may maintain the visual illuminance over 50 lx.

Preferably, but not necessarily, the light source part may include a lens part generating a white light by mixing lights emitted from the red light source, the green light source and the blue light source.

Preferably, but not necessarily, the controller may include:

a memory setting a size of current applied to the red light source, the green light source and the blue light source at each bio illuminance; and a timer in which the morning hours and the evening hours are set.

Preferably, but not necessarily, the controller may include a communication part performing communications with outside servers.

Preferably, but not necessarily, the controller may control the power part by receiving, from the server, a current control signal corresponding to the bio illuminance.

The lighting device for bright therapy and dark therapy according to the present invention has an advantageous effect in that a man's circadian rhythm can be improved by sufficiently suppressing the melatonin secretion during morning hours by matching a daily light environment affecting the man's circadian rhythm to melatonin secretion cycle, and enhancing the man's circadian rhythm by greatly increasing the melatonin secretion during evening hours.

The hitherto-mentioned advantageous effects of the present invention are not limited to those mentioned above, and other effects not mentioned herein will be clearly understood by those of ordinary skill in the art from the following description.

BRIEF DESCRIPTION OF THE DRAWINGS

The above and other objects, features and advantages of the present disclosure will become more apparent to those of ordinary skill in the art by describing in detail exemplary embodiments thereof with reference to the accompanying drawings, in which.

DETAILED DESCRIPTION OF EXAMPLE EMBODIMENTS

Figure 1:
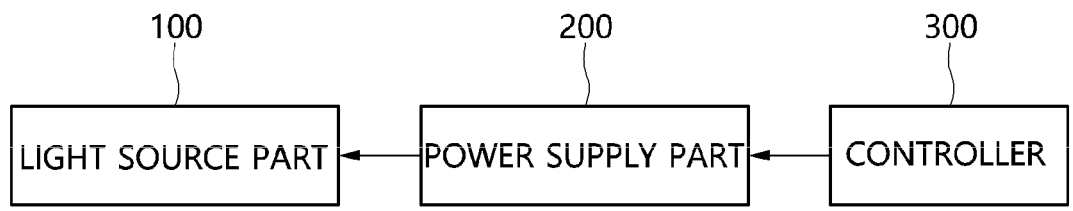
FIG. 1 is a schematic block diagram of a lighting device for bright therapy and dark therapy according to an exemplary embodiment of the present invention.

Now, some of the exemplary embodiments of the present invention will be described with the accompanying drawings. Detailed descriptions of well-known functions, configurations or constructions are omitted for brevity and clarity so as not to obscure the description of the present invention with unnecessary detail. Furthermore, throughout the descriptions, the same reference numerals will be assigned to the same elements in the explanations of the figures.

Furthermore, when it is determined that detailed descriptions of relevant known technologies may obscure the subject matter of the present invention in the description of the present invention, detailed descriptions thereof will be omitted. In addition, it should be noted that the accompanying drawings are provided only for facilitating the easy understanding of a spirit of the present invention and should not be interpreted as limiting the spirit of the present invention by the accompanying drawings.

Figure 2:
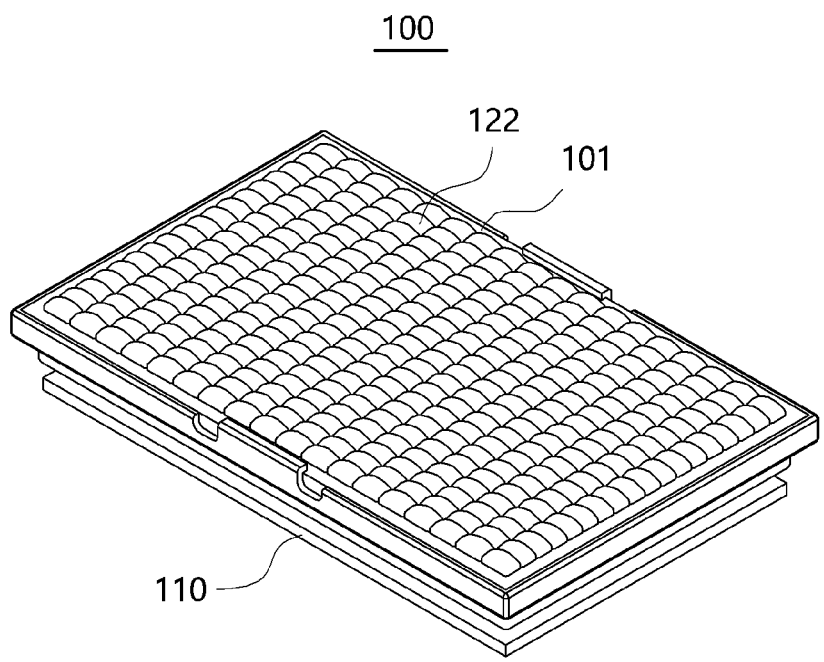
FIG. 2 is a perspective view of a light source part according to an exemplary embodiment of the present invention.
Figure 3:
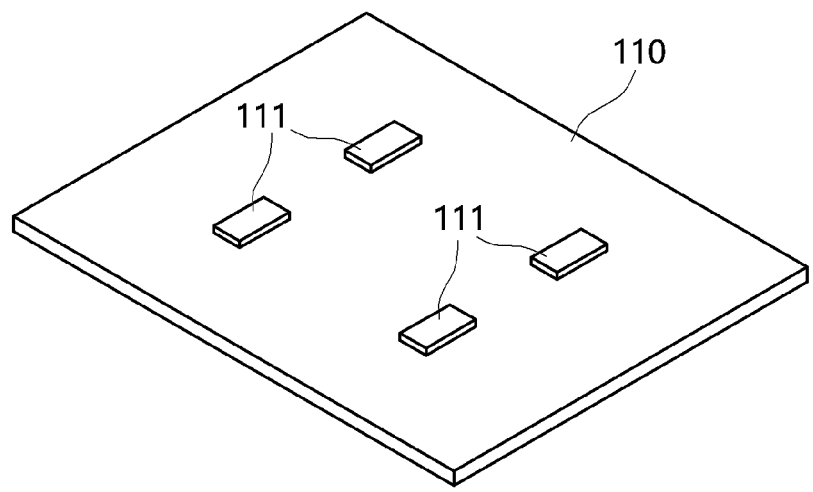
FIG. 3 is a perspective view of a light source array according to an exemplary embodiment of the present invention.
Figure 4:
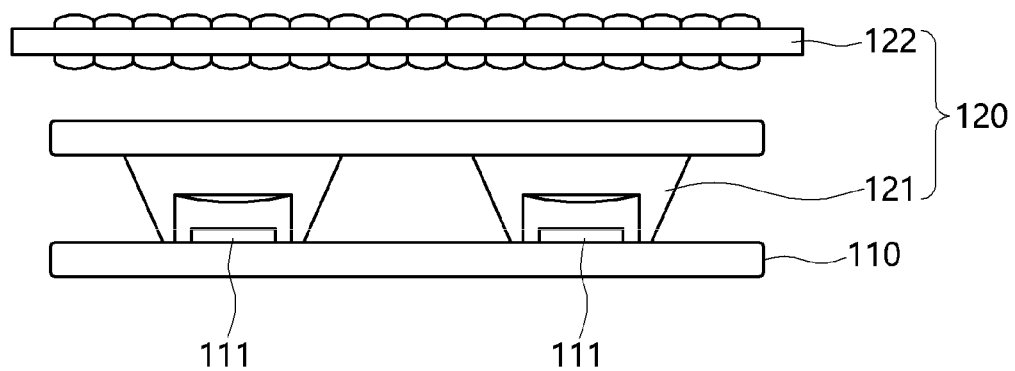
FIG. 4 is a cross-sectional view of a light source part according to an exemplary embodiment of the present invention.

FIG. 1 is a schematic block diagram of a lighting device for bright therapy and dark therapy according to an exemplary embodiment of the present invention, FIG. 2 is a perspective view of a light source part according to an exemplary embodiment of the present invention, FIG. 3 is a perspective view of a light source array according to an exemplary embodiment of the present invention, and FIG. 4 is a cross-sectional view of a light source part according to an exemplary embodiment of the present invention.

As illustrated in FIG. 1, a lighting device both for bright therapy and dark therapy according to an exemplary embodiment of the present invention may include a light source part 100, a power supply part 200, and a controller 300.

Referring to FIGS. 2, 3 and 4, the light source part 100 may include a light source array 110, a plurality of light sources 111, a lens housing 101 and a lens part 120.

The plurality of light sources 111 may include a red light source, a green light source, an orange light source, and a blue light source, and may be mounted on the light source array 110 in two columns and two rows. Here, each light source 111 may be an LED (Light Emitting Diode), but the said each light source 111 may not be limited thereto.

Although the plurality of light sources 111 may be formed with a red light source, a green light source, and a blue light source, the plurality of light sources 111 may further include an orange light source in order to increase a CRI (Color Rendering Index). In addition, the red light source, the green light source, and the orange light source excluding the blue light source may be color-conversion light sources using color conversion phosphors or quantum dots in order to further increase the CRI.

Here, the CRI may mean a degree of similarity between a color of an object viewed in natural light and a color of an object viewed under a specific illumination, and the light source part 100 according to the present invention may maintain a CRI of 80 or more.

The light source array 110 may be mounted with a plurality of light sources 111, and may be buried with a wiring for supplying a power to the plurality of light sources 111.

The lens housing 101 may be formed thereunder with an insertion groove into which a plurality of light sources 111, and may be formed thereon with an opening through which a light having passed through the plurality of light sources 111 and the lens part 120 is emitted.

The lens part 120 may be disposed at an upper surface of the light source array 110 and may be accommodated into the lens housing 101. Here, the lens housing 101 may be disposed on either side of the upper surface with hooks, and may be fixed onto the lens housing 101 by allowing the lens part 120 to be press-fitted into the hooks.

The lens part 120 may generate a white light by allowing lights emitted from a red light source, a green light source, an orange light source, and a blue light source to be mixed. Toward this end, the lens part 120 may include a total reflection lens 121 and a lens array 122.

The total reflection lens 121 may be formed with a conical shape and may be formed at an upper surface thereof with an accommodation groove into which a plurality of light sources 111 is accommodated. Furthermore, the total reflection lens 121 may be provided as many numbers as those of the plurality of light sources 111.

The said total reflection lens 121 may serve to convert a light emitted from the plurality of light sources 111 into a parallel light by allowing the light to be totally reflected.

The lens array 122 may be formed with a plate shape, and may be formed on both sides with a plurality of embossing patterns. The said lens array 122 may be disposed at an upper surface of the total reflection lens 121 and may serve to emit the parallel light emitted from the total reflection lens 121. The power supply part 200 may supply an electric power to the light source part 100, and the controller 300 may control a current supplied to the light source part 100 by controlling the power supply part 200.

Figure 5:
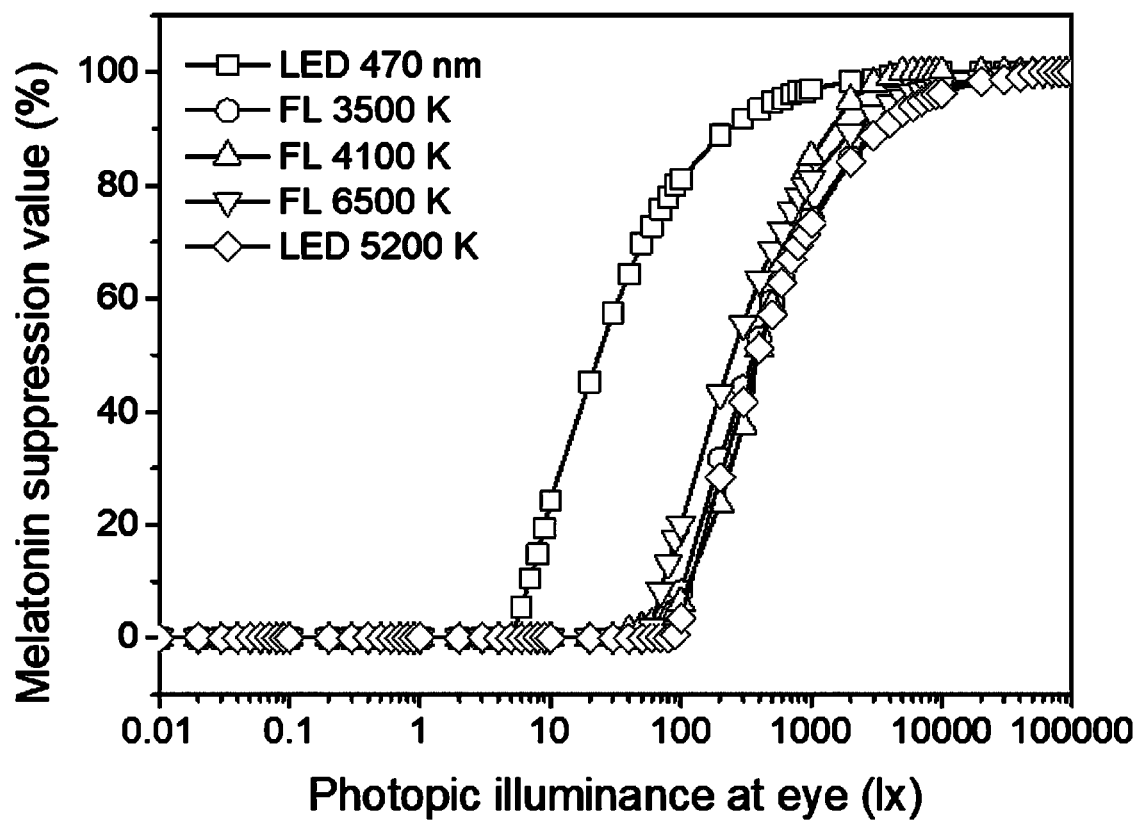
FIG. 5 is a graph illustrating a melatonin suppression value according to visual illuminance of various types of light sources.
Figure 6:
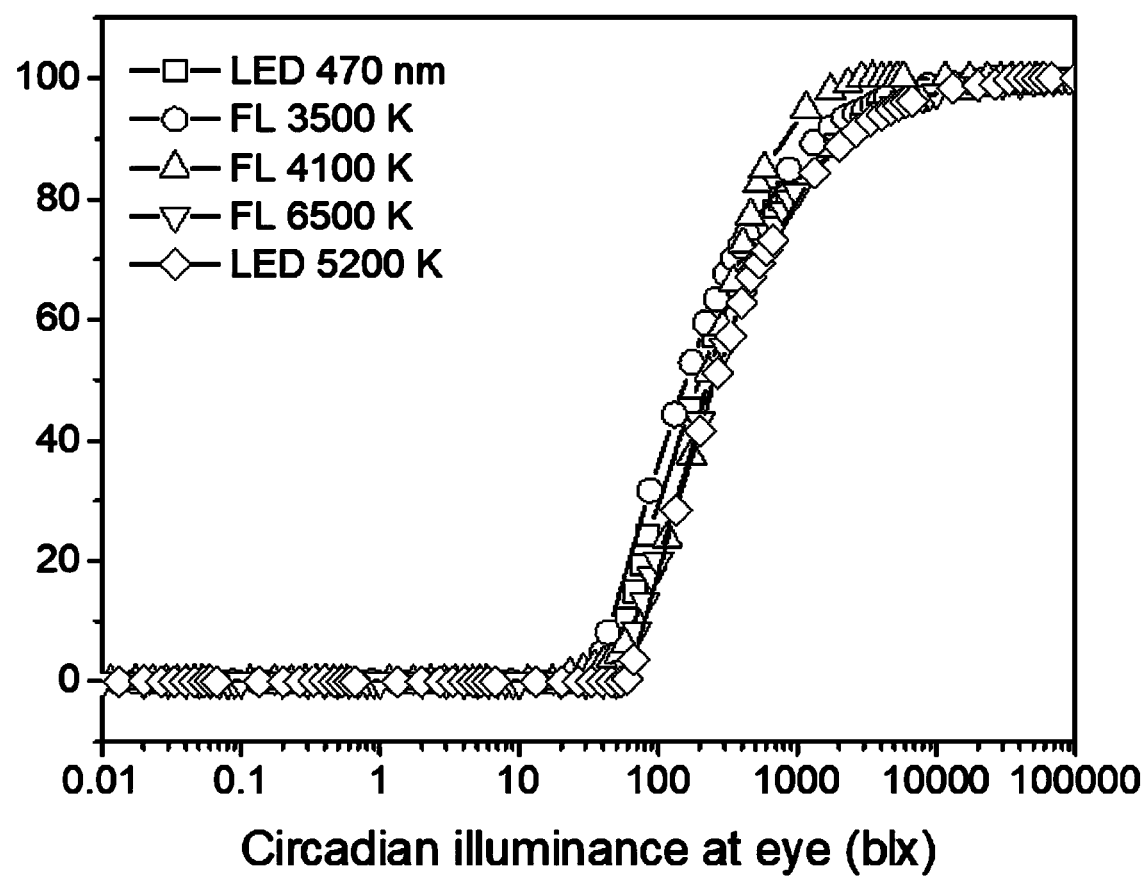
FIG. 6 is a graph illustrating a melatonin suppression value according to bio illuminance of various types of light sources.
Figure 7:
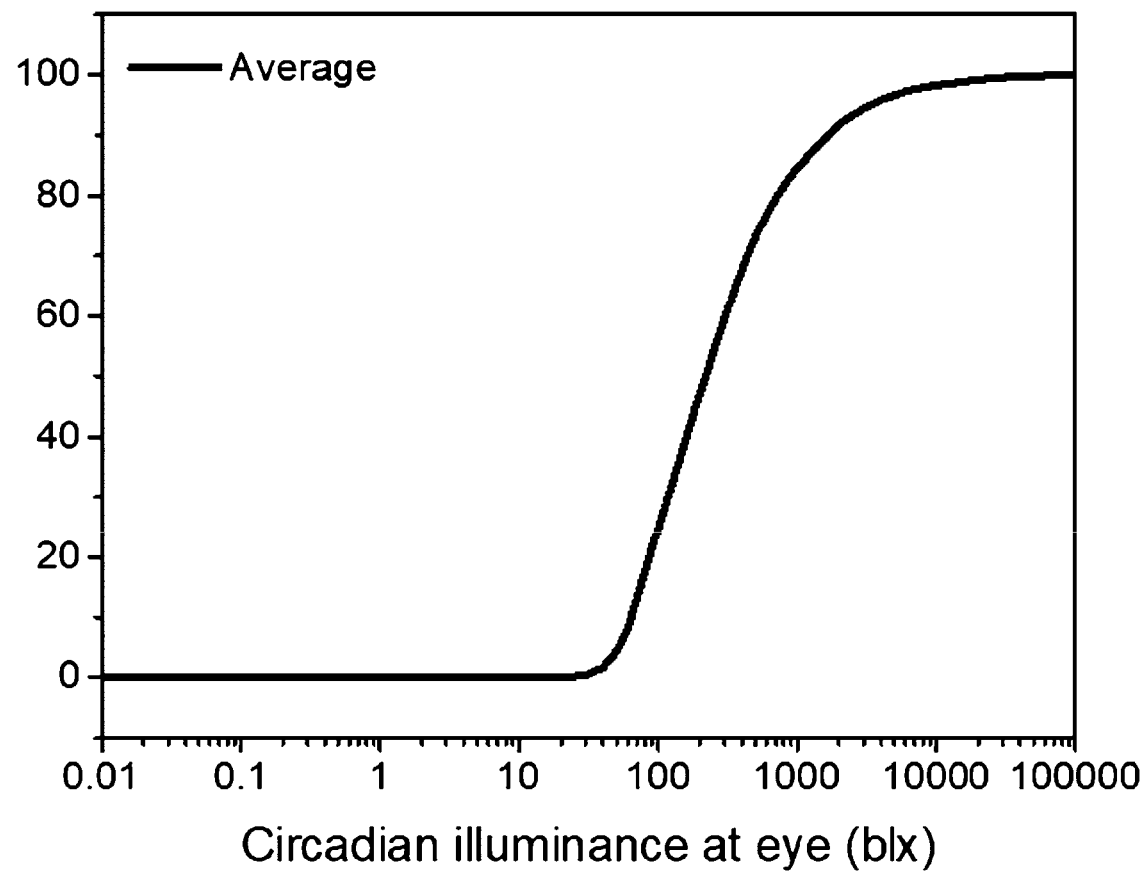
FIG. 7 is a graph illustrating an average melatonin suppression value according to bio illuminance of various types of light sources.

FIG. 5 is a graph illustrating a melatonin suppression value according to visual illuminance of various types of light sources, FIG. 6 is a graph illustrating a melatonin suppression value according to bio illuminance of various types of light sources, and FIG. 7 is a graph illustrating an average melatonin suppression value according to bio illuminance of various types of light sources.

As illustrated in FIG. 5, it may be ascertained that melatonin suppression values are different according to the type and color temperature, even if a light source emits a light having the same photopic illuminance. Therefore, there is a limit in accurately controlling the melatonin suppression values by adjusting visual illuminance.

As shown in FIG. 6, it may be ascertained that light sources emitting lights of same circadian illuminance have almost the same melatonin suppression value Irrespective of types and color temperatures thereof.

In order to clarify a relationship between a bio illuminance and a melatonin suppression value, an average melatonin suppression value derived from averaged melatonin suppression values based on various types of bio illuminances is defined by way of a graph as illustrated in FIG. 7, which is then applied to the light device for bright therapy and dark therapy according to the exemplary embodiments of the present invention.

The lighting device for bright therapy and dark therapy according to the exemplary embodiments of the present invention thus elaborated can achieve a more accurate control in controlling the melatonin suppression value because the light source part 100 can adjust a bio illuminance of emitted light.

Referring to FIG. 7, it may be ascertained that the melatonin suppression values are respectively 0.4% and 1.7% when bio-illuminances are 30 blx and 40 blx, the melatonin suppression value is 0% when bio-illuminance is 30 blx, and the melatonin suppression value is 100% when the bio illuminance is over 10000 blx.

Furthermore, it may be ascertained that the melatonin suppression value increases as a bio-illuminance increases between the bio-illuminances of 30 blx and 10000 blx.

The controller 300 may adjust the bio illuminance in such a manner that the melatonin suppression value becomes greater than or equal to a first reference value in the morning hours, and adjust the bio illuminance in such a manner that the melatonin suppression value becomes less than a second reference value in the evening hours while maintaining a visual illuminance at a certain predetermined value or higher. That is, the controller 300 in the lighting device for bright therapy and dark therapy according to the exemplary embodiments of the present invention performs a bright therapy in the morning hours and a dark therapy in the evening hours.

Here, the morning hours may mean a time zone from sun-rise to noon, and the evening hours may mean a time zone from sun-set to sun-rise the next day.

In addition, the first reference value may be a value selected from within a range of 70% to 100%, and the second reference value may be a value selected from within a range of 30% or less, but excluding zero (0). In particular, it is preferable that the first reference value be 90% and the second reference value be 10%.

For example, referring to FIG. 7, the controller 300 may emit a light having a bio illuminance of 800 blx corresponding to 70% of melatonin suppression value during the morning hours by controlling a current supplied to a plurality of light sources from the power supply part 200, and may emit a light having a bio illuminance of 100 blx corresponding to a melatonin suppression value of 20% during the evening hours.

The visual illuminance may refer to an intensity of light perceivable by the human eye, and the bio illuminance may be defined as a product of visual illuminance and CAF (Circadian Action Factor). Here, the CAF may be defined as a ratio of CER (Circadian Efficacy of Radiation relative to LER (Luminous Efficacy of Radiation).

The controller 300 may adjust the bio illuminance by controlling the visual illuminance or the CAF of light emitted from the light source part 100.

The controller 300 may simultaneously adjust the visual illuminance and bio-illuminance of light emitted from the light source part 100 based on time or external environment. To be more specific, the controller 300 may increase or decrease both the visual illuminance and bio-illuminance based on the time or external environment, where the visual illuminance may be increased, the bio-illuminance may be decreased, the visual illuminance may be decreased, or the bio-illuminance may be increased.

The controller 300 may adjust the bio-illuminance by controlling ON/OFF of the red light source, the green light source, the orange light source, and the blue light source, or alternatively may adjust the bio illuminance by controlling a current applied to the red light source, the green light source, the orange light source, and the blue light source.

That is, the controller 300 may adjust the bio-illuminance by controlling only the visual illuminance while maintaining the CAF at a predetermined level. Here, the visual illuminance is a means for controlling the bio-illumination, such that a direct factor controlling the melatonin suppression value may not be the visual illuminance but eventually the bio-illuminance.

For example, the controller 300 may apply a total of 600 mA of current to the red light source, the green light source, the orange light source, and the blue light source by dividing the same on an equal base, and then, in order to decrease the bio illumination, may apply a total of 600 mA of current to the red light source, the green light source, the orange light source, and the blue light source by dividing the same on an equal base. In this case, although the CAF may be same for the former case and the latter case, the bio illuminance becomes decreased due to the latter case being lower than the former case in terms of visual illuminance.

The controller 300 may adjust the bio illuminance by controlling an amount of current respectively applied to the red light source, the green light source, and the blue light source while the size of the current supplied to the light source part 100 is maintained at a predetermined value. That is, the controller 300 may adjust the bio illuminance by controlling only the CAF while maintaining the visual illuminance at a predetermined level. Here, the CAF is a means for controlling the bio-illumination, such that the direct factor controlling the melatonin suppression value may not be the CAF but eventually the bio-illuminance.

For example, the controller 300 may apply a current of 150 mA respectively to the red light source, the green light source, the orange light source, and the blue light source, while an amount of current applied to the light source part 100 is maintained at 600 mA, and then may apply a current respectively of 100 mA, 150 mA, 150 mA, and 200 mA to the red light source, the green light source, the orange light source, and the blue light source in order to increase the bio illumination. In this case, the bio-illumination may be increased because the latter case has a higher CAF than that of the former case.

Meanwhile, there may be a limit in controlling the bio illuminance by controlling only the visual illuminance while the CAF is maintained at a predetermined level. That is, although the melatonin suppression value may become decreased when the bio illuminance is lowered by decreasing the visual illuminance during the evening hours, there may rise a problem in visually viewing an object due to the decreased visual illuminance.

As a result, it is preferable for the controller 300 to maintain a visual illuminance at over 50 lx when the bio-illuminance is adjusted by controlling the visual illuminance during the evening hours. Toward this end, the controller 300 may adjust the bio illuminance by controlling the visual illuminance or the CAF in the morning hours and adjust the bio illuminance by controlling the CAF during evening hours.

The controller 300 may include a memory in which a size of current applied to each light source 111 is set for each bio illuminance, and a timer in which the morning hours and the evening hours are set.

As a result, the controller 300 may apply, to each light source 111, a current corresponding to a bio illuminance in which the melatonin suppression value is greater than or equal to a first reference value in the morning hours using the timer and the memory, and may apply, to each light source 111, a current corresponding to the bio illuminance in which the melatonin suppression value becomes less than a second reference value during evening hours.

The controller 300 may include a communication part for performing a communication with an external server. In this case, the above-mentioned memory and timer may be provided on a server. The said server may apply in the morning hours, to the controller 300, a current control signal corresponding to the bio-illuminance in which the melatonin suppression value is greater than or equal to a first reference value, and may apply in the evening hours, to the controller 300, a current control signal corresponding to bio illuminance in which the melatonin suppression value is less than a second reference value. Thereafter, the controller 300 may control the power supply part 200 by receiving a current control signal from a server through a communication part.

As noted above, the lighting device for bright therapy and dark therapy according to the exemplary embodiments of the present invention can sufficiently suppress the melatonin secretion in the morning hours by adjusting a daily light environment that affects a man's circadian rhythm to a melatonin secretion cycle, and can enhance the man's circadian rhythm in the evening hours by greatly increasing the melatonin secretion.

The exemplary embodiments and the accompanied drawings described in the present specification are merely illustrative of some of the technical spirits included in the present invention. Thus, the exemplary embodiments disclosed in the present specification are not intended to limit the technical spirits of the present invention but to explain the same, and therefore, it should be obvious that the scope of the technical spirits of the present invention is not limited by these embodiments. Within the scope of the technical spirits included in the specification and drawings of the present invention, it should be interpreted that modifications and specific exemplary embodiments easily inferred by those skilled in the art are all included in the scope of the present invention.

What is claimed is:

1. A lighting device for bright therapy and dark therapy, the lighting device comprising:
   a light source part including a red light source, a green light source and a blue light source;
   a power supply part supplying a power to the light source part; and
   a controller adjusting, by controlling the power supply part, a bio illuminance to allow melatonin suppression value to exceed a first reference value during morning hours and to allow the melatonin suppression value to be less than a second reference value while maintaining a visual illuminance over a predetermined value during evening hours,
   wherein the controller adjusts the bio illuminance by controlling a size of current respectively applied to the red light source, the green light source and the blue light source while the size of the current supplied to the light source part is maintained at a predetermined value.

2. The lighting device of claim 1, wherein the controller adjusts a bio illumination by controlling a visual illumination or a CAF (Circadian Action Factor) of light emitted from the light source part.

3. The lighting device of claim 1, wherein the controller adjusts a bio illumination by controlling a visual illumination or a CAF of light emitted from the light source part during the morning hours and by controlling a CAF of light emitted from the light source part during the evening hours.

4. The lighting device of claim 1, wherein the controller adjusts the bio illuminance by controlling ON/OFF of the red light source, the green light source and the blue light source, or adjusting the bio illuminance by controlling a current applied to the red light source, the green light source and the blue light source.

5. The lighting device of claim 1, wherein the light source part further includes an orange light source.

6. The lighting device of claim 1, wherein the first reference value is a value selected from within a range of 70%-100%, and the second reference value is a value selected from within a range less than 30% or less, but excluding 0 (zero).

7. The lighting device of claim 1, wherein the controller maintains the visual illuminance over 50 lx.

8. The lighting device of claim 1, wherein the light source part includes a lens part generating a white light by mixing lights emitted from the red light source, the green light source and the blue light source.

9. The lighting device of claim 1, wherein the controller includes:
   a memory setting the size of current applied to the red light source, the green light source and the blue light source at each bio illuminance; and
   a timer in which the morning hours and the evening hours are set.

10. The lighting device of claim 1, wherein the controller includes a communication part performing communications with outside servers.

11. The lighting device of claim 10, wherein the controller controls the power part by receiving, from the outside servers, a current control signal corresponding to the bio illuminance.

* * * * *